(12) United States Patent
Hayden et al.

(10) Patent No.: US 11,035,836 B2
(45) Date of Patent: Jun. 15, 2021

(54) METHODS OF GENERATING AND CORROSION TESTING AQUEOUS GAS STREAMS PREPARED FROM AQUEOUS ACID AND SALT PRECURSOR SOLUTIONS

(71) Applicant: Saudi Arabian Oil Company, Dhahran (SA)

(72) Inventors: Steven C. Hayden, Boston, MA (US); Timothy J. Kucharski, Belmont, MA (US); Michele L. Ostraat, Somerville, MA (US); Rachael O. Grudt, Medford, MA (US); James P. Mullahoo, Milford, MA (US)

(73) Assignee: Saudi Arabian Oil Company, Dhahran (SA)

( * ) Notice: Subject to any disclaimer, the term of this patent is extended or adjusted under 35 U.S.C. 154(b) by 349 days.

(21) Appl. No.: 16/050,245

(22) Filed: Jul. 31, 2018

(65) Prior Publication Data
US 2020/0041473 A1 Feb. 6, 2020

(51) Int. Cl.
*G01N 17/02* (2006.01)
*G01N 33/00* (2006.01)

(52) U.S. Cl.
CPC ................. *G01N 33/0004* (2013.01)

(58) Field of Classification Search
CPC ............ G01N 17/02; G01N 33/0004
(Continued)

(56) References Cited

U.S. PATENT DOCUMENTS 3,323,873 A * 6/1967 Rinkes .............. C01B 32/50
422/618
4,241,951 A 12/1980 Hard
(Continued)

FOREIGN PATENT DOCUMENTS

CN 103954664 A 7/2014
GB 2159507 A 12/1985
(Continued)

OTHER PUBLICATIONS

Morris, D. R. et al, Journal of the Electrochemical Society 1980, 127, 1228-1235.*
(Continued)

*Primary Examiner* — Arlen Soderquist
(74) *Attorney, Agent, or Firm* — Dinsmore & Shohl LLP

(57) ABSTRACT

Embodiments of methods for producing and testing aqueous gas streams within a self-pressurized flow cell are disclosed. The aqueous gas streams comprise mixtures of aqueous salt precursor and aqueous acid precursor that are mixed in-line and introduced to the self-pressurized flow cell to produce aqueous gases. Once in the self-pressurized flow cell, the precursor mixture formed from the mixed aqueous salt precursor and the aqueous acid precursor may react with the sample. Both the sample and the reacted aqueous solution may be subjected to a variety of real-time tests, such electrochemical tests and in line characterization techniques. These embodiments allow for the concentrations of the aqueous salt precursor and the aqueous acid precursor to be accurately and precisely maintained while allowing for increased safety when handling and testing the various toxic aqueous gas streams produced.

21 Claims, 6 Drawing Sheets

(58) Field of Classification Search
USPC .......................................... 422/53; 436/6, 9
See application file for complete search history.

(56) References Cited

U.S. PATENT DOCUMENTS

| | | | |
|---|---|---|---|
| 4,683,035 A * | 7/1987 | Hunt | G01N 17/00 204/404 |
| 4,856,587 A | 8/1989 | Nielson | |
| 4,888,160 A | 12/1989 | Kosin et al. | |
| 5,971,368 A | 10/1999 | Nelson et al. | |
| 6,235,641 B1 | 5/2001 | Christenson | |
| 6,468,953 B1 | 10/2002 | Hitchems et al. | |
| 6,648,307 B2 | 11/2003 | Nelson et al. | |
| 9,873,951 B2 | 1/2018 | Kaczur et al. | |
| 2002/0153907 A1 | 10/2002 | Yang et al. | |
| 2009/0078415 A1 | 3/2009 | Fan et al. | |
| 2010/0126859 A1 | 5/2010 | Yang et al. | |
| 2010/0219373 A1 | 9/2010 | Seeker et al. | |
| 2011/0024361 A1 | 2/2011 | Schwartzel et al. | |
| 2011/0066388 A1 | 3/2011 | Snelling et al. | |
| 2012/0298522 A1 | 11/2012 | Shipchandler et al. | |
| 2014/0220699 A1 | 8/2014 | Pudil | |
| 2014/0318959 A1 | 10/2014 | Yang et al. | |
| 2015/0267309 A1 | 9/2015 | Kaczur et al. | |

FOREIGN PATENT DOCUMENTS

| | | | |
|---|---|---|---|
| JP | 6-27076 | * | 2/1994 |
| JP | 2009056418 A | | 3/2009 |
| WO | 2009/015318 | * | 1/2009 |

OTHER PUBLICATIONS

Bacarella, A. L. et al, Journal of the Electrochemical Society 1965, 112, 546-553.*
Harrar, J. E. et al, Report UCRL-52376, 1977, 28 pages.*
Heaton, W. Et al, British Journal of Corrosion 1978, 13, 57-63.*
Bech-Nielsen, G. et al, Corrosion Science 1994, 36, 759-771.*
Hernandez, R. et al, ECS Transactions 2007, 3, 181-198.*
Farelas, F. et al, Corrosion Science 2010, 52, 509-517.*
Sanni, O. et al, Corrosion 2015, Paper 5916, 15 pages.*
Jungjohann, K. L. et al, Microscopy and Microanalysis 2016, 22, suppliment 3, 1564-1565.*
Bukuaghangin, O. et al, Journal of Petroleum Science and Engineering 2016, 147, 699-706.*
Aoyama, T. et al, Corrosion Science 2017, 127, 131-140.*
International Search Report and Written Opinion pertaining to Application No. PCT/US2019/042548 dated Jan. 29, 2020.
Tillier et al., "Electrochemical Flow-Cell Setup for in Situ X-ray Investigations II. Cell for SAXS on a Multi-Purpose Laboratory Diffractometer", Journal of the Electrochemical Society, 163 (10), H913-H920, Aug. 5, 2016.
Examination Report dated Aug. 9, 2020 pertaining to GCC Patent Application No. 2019-38024.
Second Examination Report dated Feb. 9, 2021 pertaining to GCC Patent Application No. 2019-38024 filed Jul. 31, 2019.

* cited by examiner

METHODS OF GENERATING AND CORROSION TESTING AQUEOUS GAS STREAMS PREPARED FROM AQUEOUS ACID AND SALT PRECURSOR SOLUTIONS

TECHNICAL FIELD

Embodiments of the present disclosure generally relate to methods of generating and testing dissolved gases in aqueous liquid streams and more specifically relate to mixing an aqueous acid precursor solution and an aqueous salt precursor solution at an in-line mixing location under pressure containment to generate dissolved aqueous gas and introducing the aqueous mixture to a self-pressurizing flow cell, and then exposing the materials under study to the aqueous gas stream within the self-pressurized flow cell.

BACKGROUND

The oil and gas industry struggles with the effects of dissolved gases, such as carbon dioxide ($CO_2$) and hydrogen sulfide ($H_2S$), which lead to pipeline degradation and corrosion when liquid and gases that contain $CO_2$, $H_2S$, or mixtures thereof are transported. Consequently, understanding the corrosive mechanism of $CO_2$ and $H_2S$ is important for pipeline preservation, as a deeper understanding of this mechanism in different conditions allows for improved pipeline servicing. It is beneficial for the concentrations of the dissolved aqueous gases to be chosen, controlled, and accurately and precisely maintained when the dissolved aqueous gases are tested, particularly when these materials are also toxic. Concentration stability is especially imperative when analyzing how dissolved aqueous gases interact with samples, as concentrations of single and mixed gases can impact materials differently, and changing one without affecting the concentration of other dissolved species can be challenging with other methods. Further, some dissolved aqueous gases must be handled safely so that exposure to the environment and humans can be limited. However, current methods of producing dissolved aqueous gases make it difficult to both maintain the desired concentrations of the dissolved aqueous gases and limit the atmospheric exposure of the corrosive and toxic gas species while concurrently allowing for real-time electrochemical measurements.

SUMMARY

Accordingly, ongoing needs exist for methods of producing and testing dissolved aqueous gases in which the concentrations of the dissolved aqueous gases are maintained while also limiting the atmospheric exposure of the toxic gas species without the need for gas feedstocks. The present methods for producing dissolved aqueous gases meet these needs and show a marked improvement in maintaining concentrations of the dissolved aqueous gas species while minimizing occupational and environmental safety issues. Controlling the concentrations of the dissolved aqueous gas species provides safer methods for handling toxic dissolved aqueous gas species, such as $H_2S$, as the species are initially generated using a less-hazardous aqueous salt precursor solution and subsequently neutralized inside a fully contained apparatus. A controlled concentration of the dissolved aqueous gas species further provides for more stable testing conditions in which a sample may be analyzed in the presence of one or more of the dissolved gas species.

According to at least one embodiment of the present disclosure, a method for generating an aqueous gas stream is provided. The method includes preparing an aqueous acid precursor solution and an aqueous salt precursor solution. The aqueous acid and aqueous salt precursor solutions are fed through individual inlet pumps upstream of the in-line mixing location. The aqueous acid and aqueous salt precursor solutions are combined at an in-line mixing location to create the precursor mixture, which is then introduced through an inlet tube to a self-pressurized flow cell downstream of the in-line mixing location. The combination of the two precursor mixtures results in a reaction to form aqueous gas. The inlet tube is surrounded by a sealing mechanism, which maintains pressure within the self-pressurized flow cell. Once the precursor mixture is introduced to the self-pressurized flow cell the aqueous gas stream produces a pressure level that correlates to the amount of dissolved gas produced within the self-pressurized flow cell. Finally, the aqueous gas stream is transferred from the self-pressurized flow cell through an outlet tube. The pressure in the outlet tube is maintained by an adjacent pressure regulator that prevents depressurization of the self-pressurized flow cell.

The aqueous acid precursor solution may comprise any strong acid, including sulfuric acid, hydrogen iodide, hydrogen bromide, perchloric acid, hydrogen chloride, chloric acid, nitric acid, and combinations thereof. The aqueous salt precursor solution may comprise any salt including, but not limited to, sodium sulfide, sodium sulfate, sodium carbonate, magnesium chloride, calcium chloride, potassium chloride, and combinations thereof. Both the aqueous acid precursor solution and the aqueous salt precursor solution may have concentrations ranging from 0 M to saturated conditions and preferably between 5 µM and 10 M or between 100 µM and 100 mM.

Additionally, according to other embodiments, the aqueous gas stream is further subjected to in-line effluent characterizations that can occur in real time within and outside the self-pressurized flow cell. These and other embodiments are described in more detail in the following Detailed Description.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Specific embodiments of the present application will now be described. The disclosure may, however, be embodied in different forms and should not be construed as limited to the embodiments set forth in this disclosure. Rather, these embodiments are provided so that this disclosure will be thorough and complete, and will fully convey the scope of the subject matter to those skilled in the art.

In some embodiments, "aqueous gas" may be defined as any gas present in a physical solution, such as a liquid. Aqueous gases can be naturally occurring and found in water used in production of oil from underground formations.

In some embodiments, "self-pressurized flow cell" may be defined as an air-tight, fully self-contained apparatus suitable for receiving various precursor mixtures. In further embodiments, the self-pressurized flow cell may be an electrochemical cell in which electrochemical tests are conducted in self-pressurized conditions. The self-pressurized flow cell may be comprised of glass, such as silica, borosilicate, quartz glass, or other commercial glasses. Further, the self-pressurized flow cell may be comprised of plastic, such as elastomers, rubber, polyamides, commonly-used polymers, or other commercial plastics. The self-pressurized flow cell may also be comprised of plastic parts that are printed with a 3D printer.

Figure 1:
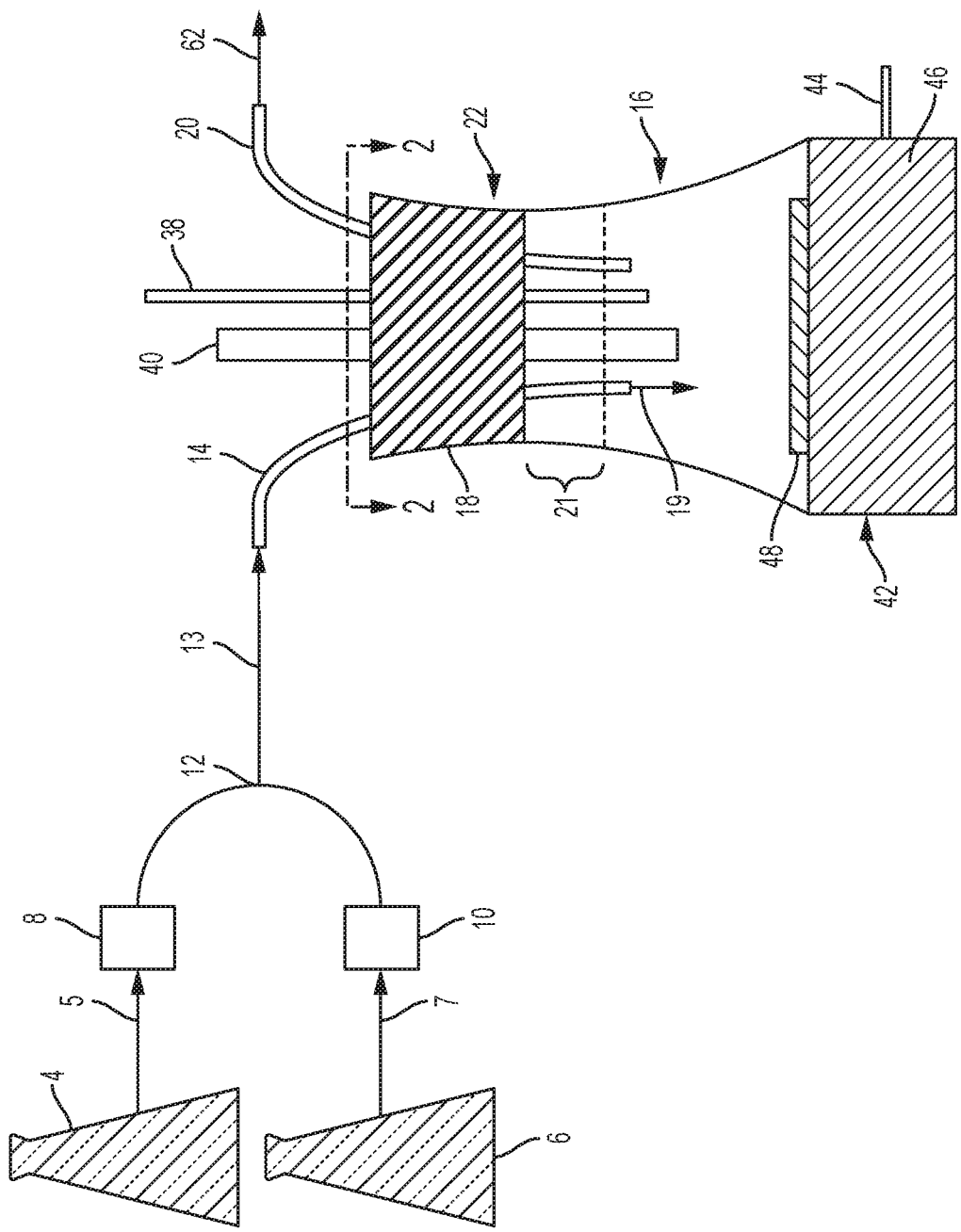
FIG. 1 is an illustration depicting one embodiment of the self-pressurized flow cell.

Referring now to FIG. 1, which depicts one embodiment of an apparatus 2 used to produce an aqueous gas solution 19 within a self-pressurized flow cell 16. The method comprises mixing an aqueous acid precursor solution 5 from an acid precursor source 4 and an aqueous salt precursor solution 7 from a salt precursor source 6 at an in-line mixing location 12. The aqueous acid precursor solution 5 may be comprised of a strong acid having a $pK_a$ of less than or equal to $-1.74$, such that all protons capable of being released by the acid in water will be released without any partitioning between the acid and water. These acids may include sulfuric acid, hydrogen iodide, hydrogen bromide, perchloric acid, hydrogen chloride, chloric acid, nitric acid, and combinations thereof. The use of weak acids may also be possible depending on the conditions desired within the self-pressurized flow cell 16.

The aqueous salt precursor solution 7 may be comprised of any salt including, but not limited to, sodium sulfide, sodium sulfate, sodium carbonate, magnesium chloride, calcium chloride, potassium chloride, and combinations thereof. The aqueous acid precursor solution 5 is fed through an aqueous acid inlet pump 8, which is upstream of the in-line mixing location 12. Similarly, the aqueous salt precursor solution 7 is fed through an aqueous salt inlet pump 10, which is also upstream of the in-line mixing location 12. The inlet pumps (8 and 10) are capable of 0.001-100 mL/min flow rates in 0.001 mL/min increments. Further flow rates of the inlet pumps (8 and 10) may range from 0.001-75 mL/min, 0.001-50 mL/min, 0.001-25 mL/min, 0.001-10 mL/min, 0.002-10 mL/min, 0.003-10 mL/min, 0.004-10 mL/min, 0.005-10 mL/min, 0.01-10 mL/min, 0.025-10 mL/min, 0.05-10 mL/min, 0.075-10 mL/min, 0.1-10 mL/min, 0.25-10 mL/min, 0.5-10 mL/min, 0.75-10 mL/min, 1-10 mL/min, 2-10 mL/min, 3-10 mL/min, 4-10 mL/min, 5-10 mL/min, 5-9 mL/min, 5-8 mL/min, and 5-7 mL/min.

The inlet pumps (8 and 10) are capable of providing a delivery pressure of 0-400 bar. Further delivery pressures of the inlet pumps (8 and 10) may range from 0-350 bar, 0-300 bar, 0-250 bar, 0-200 bar, 0-150 bar, 0-100 bar, 1-100 bar, 1-75 bar, 1-50 bar, 1-25 bar, 5-75 bar, 5-50 bar, 5-25 bar, and 10-25 bar.

In some embodiments, the volumetric ratio of aqueous acid precursor solution 5 to aqueous salt precursor solution 7 is 1:1. Further volumetric ratios between the acid precursor solution 5 to aqueous salt precursor solution 7 may range from 1:10,000; 1:7,500; 1:5,000; 1:2,500; 1:1,000; 1:750; 1:500; 1:250; 1 1:100; 1:50; 1:20; 1:10; 1:5; 1:4; 1:3; and 1:2; or from 10,000:1; 7,500:1; 5,000:1; 2,500:1; 1,000:1; 750:1; 500:1; 250:1; 100:1; 50:1; 20:1; 10:1; 5:1; 4:1; 3:1; and 2:1.

Once the aqueous acid precursor solution 5 and the aqueous salt precursor solution 7 have been mixed at the in-line mixing location 12, the two precursor solutions form a precursor mixture 13. The precursor mixture 13 is then introduced through an inlet tube 14 to the self-pressurized flow cell 16 downstream of the in-line mixing location 12 to form an aqueous gas solution 19. The inlet tube 14 is surrounded by a sealing mechanism 18, which maintains pressure within the self-pressurized flow cell 16. A gas headspace 21 develops over the aqueous gas solution 19 formed within the self-pressurized flow cell 16. Once the aqueous gas solution 19 has developed within the self-pressurized flow cell 16, the aqueous gas solution 19 may react with a sample 48. A reacted aqueous gas stream 62 that contains precursor mixture 13 minus the gas headspace 21 plus any corrosion products that may be evolved from the sample 48 is then formed and exits the self-pressurized flow cell 16 via an outlet tube 20. The aqueous gas solution 19 and the headspace 21 produces a pressure level that correlates to the amount of dissolved aqueous gas produced in the self-pressurized flow cell 16.

The pressure within the self-pressurized flow cell 16 may range from below ambient pressure (i.e., 1 atmosphere) to the absolute pressure limit of the self-pressurized flow cell 16, which may be higher than the saturation concentrations at ambient pressure. The aqueous acid precursor solution 5 may be concentrated in the range from 5 µM to 10 M, from 100 µM to 100 mM, or from any other suitable intermediate values thereof. Likewise, the aqueous salt precursor solution 7 may be concentrated in the range from 5 µM to 10 M, from 100 µM to 100 mM, or from any other suitable intermediate values thereof.

After the aqueous gas solution 19 is exposed to the sample 48, the reacted aqueous gas stream 62 is removed from the self-pressurized flow cell 16 through an outlet tube 20. The pressure in the outlet tube 20 may be further controlled and maintained by various pressure regulators, described in greater detail below, which reduce depressurization of the self-pressurized flow cell 16.

While the aqueous gas solution 19 is present in the self-pressurized flow cell 16, sample 48 may be subjected to a variety of in situ electrochemical measurements, including linear polarization resistance measurements, open circuit potential measurements, and electrochemical impedance spectroscopy, as well as weight-loss measurements. The reacted aqueous gas stream 62 may be subjected to additional testing, including pH measurements, ultraviolet-visible (UV-VIS) spectroscopy, Fourier transform infrared spectroscopy, attenuated total reflection infrared spectroscopy, optical spectrometry, or inductively coupled plasma (ICP) atomic emission spectroscopy after the reacted aqueous gas stream 62 has been removed from the self-pressurized flow cell 16.

Figure 2:
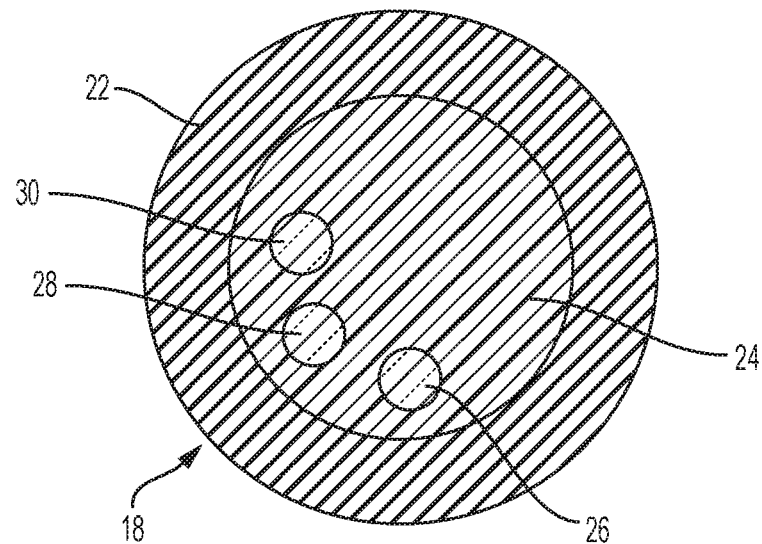
FIG. 2 is a top view depicting one embodiment of a sealing mechanism.
Figure 3:
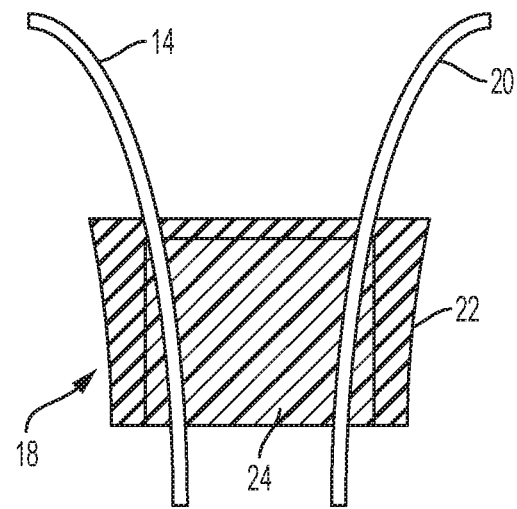
FIG. 3 is a cross-sectional view of one embodiment of a sealing mechanism.

Referring now to FIGS. 2 and 3, once the precursor mixture 13 is introduced to the self-pressurized flow cell 16, the sealing mechanism 18, according to one embodiment, maintains pressure within the self-pressurized flow cell 16. The sealing mechanism 18 may comprise an outer portion 22 and an inner portion 24. The outer portion 22 of the sealing mechanism 18 may comprise a stopper made from ethylene propylene diene monomer (EPDM) rubber, silicone rubber, neoprene rubber, pure gum rubber, natural rubber, butyl rubber, nitrile rubber, or any other suitable rubber or non-rubber materials. The inner portion 24 of the sealing mechanism 18 may comprise a plastic rod, such as a PolyEtherEtherKetone (PEEK) rod.

The outer portion 22 may be modified by drilling a hole through its middle. The configuration allows the inner portion 24 to be received into the outer portion 22 of the sealing mechanism 18. In this embodiment, the inner portion 24 is made from a substantially sturdier material than the outer portion 22. The inner portion 24 prevents the outer portion 22 from warping, as the sealing mechanism 18 may further comprise a plurality of ports. These ports may be formed by a drilling process that may warp the outer portion 22 and thereby attenuate the liquid flow through the tubes if the ports are drilled directly into the outer portion 22, which is comprised from a more malleable material than the inner portion 24. These ports may comprise an inlet port 26, an outlet port 28, and an injection port 30. The inlet tube 14 is inserted into the inlet port 26 in order to allow the precursor mixture 13 to enter the self-pressurized flow cell 16. Similarly, the outlet tube 20 is inserted into the outlet port 28 in order to allow the reacted aqueous gas stream 62 to exit the self-pressurized flow cell 16.

Figure 8:
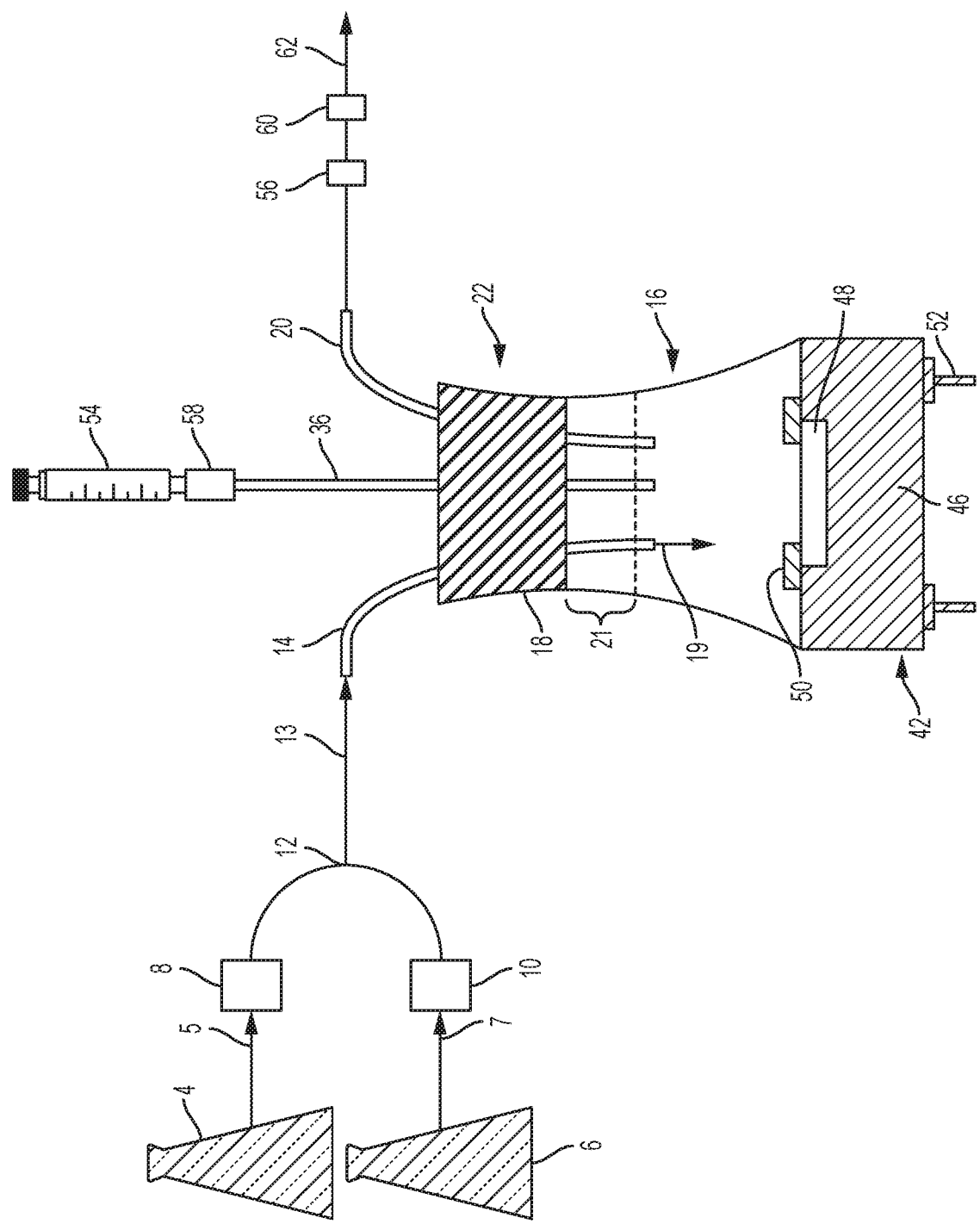
FIG. 8 is an illustration depicting another embodiment of the self-pressurized flow cell.

Referring now to FIG. 8, the outlet tube 20 may comprise multiple embodiments. In one embodiment, the outlet tube 20 may be left open and exposed to an external atmosphere by employing a tube that has a high surface area to volume ratio. This surface area to volume ratio ensures that the pressure drop along the outlet tube 20 is significant enough so as to prevent the depressurization of the self-pressurized flow cell 16.

In another embodiment, the outlet tube 20 may comprise one or more pressure regulating devices, such as an outlet pump 56 and/or a backpressure regulator 60. In this embodiment, the outlet pump 56 rate may be set to the sum of the rate of the two inlet pumps (8 and 10), thereby ensuring that a constant volume of aqueous gas solution 19 is maintained within the self-pressurized flow cell 16. In a further embodiment, the outlet tube 20 may additionally comprise a backpressure regulator 60 in addition to the outlet pump 56 so as to further ensure a maintained flow rate of the precursor mixture 13 within the self-pressurized flow cell 16.

Commercial examples of the outlet variable pressure control device 56 may include the Asia Pressure Controller by Syrris Ltd.®, the KBP, KFB, KCB, or KPB series of regulators from Swagelok®; or the 54-2100 or 26-1700 Series Control Pressure Regulators by TESCOM Corp.®. Commercial examples of the backpressure regulator 60 may include the ABP3 and ABP1 series back pressure regulators by the Parker Hannifin Corporation®.

Referring again to FIGS. 2 and 3, after all necessary components are inserted into the ports (26, 28, and 30) located on the inner portion 24 of the sealing mechanism 18, the top surface of the sealing mechanism 18 may be covered with a sealant. The sealant may seal the junctions between the inner portion 24 and the outer portion 22 and also seals between the inner portion 24 and the various ports (26, 28, and 30) to ensure that pressure is maintained within the self-pressurized flow cell 16. The sealant may comprise epoxy, liquid cement, glue, or any other suitable materials.

Once the sealing mechanism 18 is inserted into the top of the self-pressurized flow cell 16, the sealing mechanism 18 allows the self-pressurized flow cell 16 to self-pressurize to the appropriate pressure in accordance with the concentration of precursor mixture 13 introduced in the self-pressurized flow cell 16.

Figure 4:
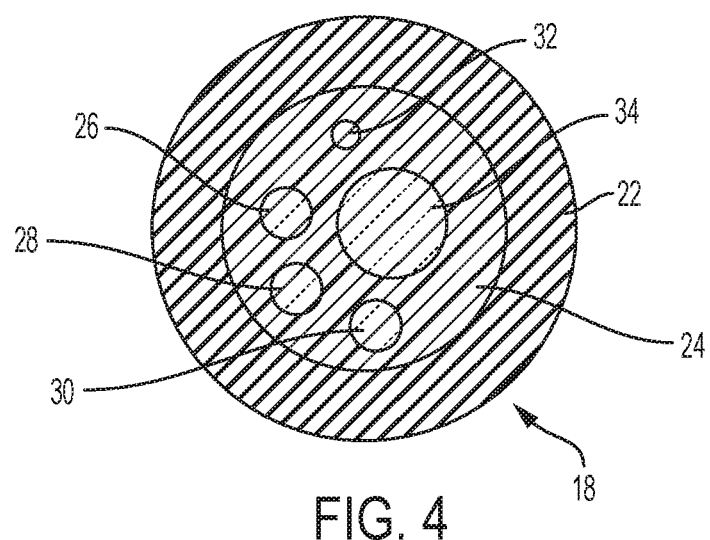
FIG. 4 is a top view depicting another embodiment of a sealing mechanism.
Figure 5:
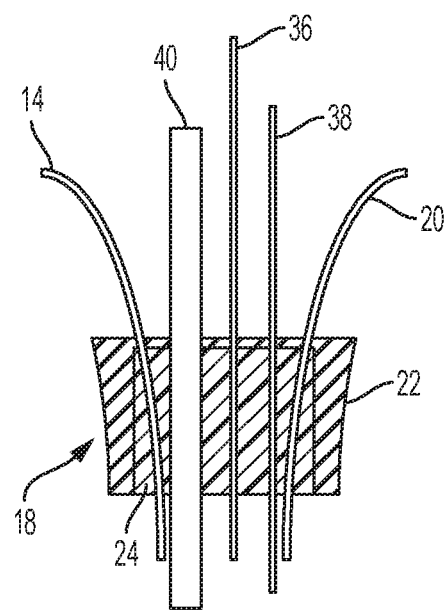
FIG. 5 is a cross-sectional view of another embodiment of a sealing mechanism.

Referring now to FIGS. 4 and 5, which depict another embodiment of the sealing mechanism 18 used to maintain the pressure within the self-pressurized flow cell 16. This embodiment of the sealing mechanism 18 may be used during various electrochemical tests. Similar to the above-detailed embodiment of the sealing mechanism 18, this embodiment of the sealing mechanism 18 further comprises an inner portion 24 with inlet port 26, an outlet port 28, and an injection port 30. The injection port 30 may receive a supplemental feed tube (36 in FIG. 8) that allows amounts of the aqueous acid precursor solution 5 or the aqueous salt precursor solution 7 to be injected directly into the self-pressurized flow cell 16. The supplemental feed tube 36 may be attached to a syringe (54 in FIG. 8), which may be filled with specified amounts of the aqueous acid precursor solution 5 or the aqueous salt precursor solution 7. This embodiment allows for the aqueous acid precursor solution 5 or the aqueous salt precursor solution 7 to be introduced into the self-pressurized flow cell 16 faster than the inlet pumps (8 and 10) provide, as the aqueous acid precursor solution 5 or the aqueous salt precursor solution 7 are being directly injected into the self-pressurized flow cell 16.

This embodiment further provides for accurate, precise, and controlled addition of additional amounts of aqueous acid precursor solution 5 or aqueous salt precursor solution 7 into the self-pressurized flow cell 16. This embodiment of the sealing mechanism 18 is especially desirable during short-term testing or experimentation where initial time points for introduction of the aqueous acid precursor solution 5 or the aqueous salt precursor solution 7 is critical. The injection port 30 may further include a backflow prevention valve (58 in FIG. 8) to ensure that the injection port 30 does not affect the sealing mechanism 18 of the self-pressurized flow cell 16. As described below, the volume of the injections via the injection port 30 may be adjusted to achieve the desired concentrations of the aqueous acid precursor solution 5 or the aqueous salt precursor solution 7 and be sufficient to fill the self-pressurized flow cell 16 to a volume at which an electrochemical circuit may be completed.

In some embodiments, the salt precursor 7 is introduced to the self-pressurized flow cell 16 as the bulk of the total volume (i.e., ~99%) before the self-pressurized flow cell 16 is sealed. The self-pressurized flow cell 16 is then sealed, and a concentrated acid precursor solution 5 is injected into the self-pressurized flow cell 16. This process helps ensure that the internal pressure of the self-pressurized flow cell 16 is not artificially inflated.

In other embodiments, the sealing mechanism 18 of FIGS. 1, 4, and 5 may include a plurality of additional ports that facilitate electrochemical testing within the self-pressurized flow cell 16. In addition to the inlet port 26, the outlet port 28, and the injection port 30, this sealing mechanism 18 may further include a counter electrode port 32 and a reference electrode port 34. In this embodiment, which is suitable for electrochemical testing, a counter electrode 38 is inserted into the counter electrode port 32 and a reference electrode 40 is inserted into the reference electrode port 34.

Figure 6:
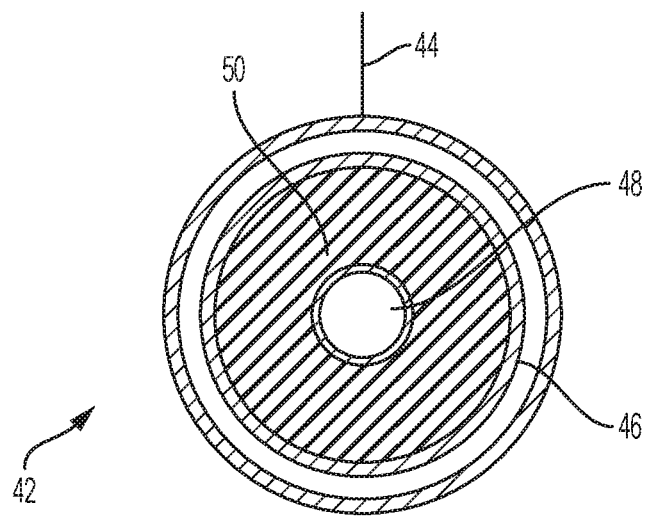
FIG. 6 is a top view of an embodiment of an electrochemical cell base.
Figure 7:
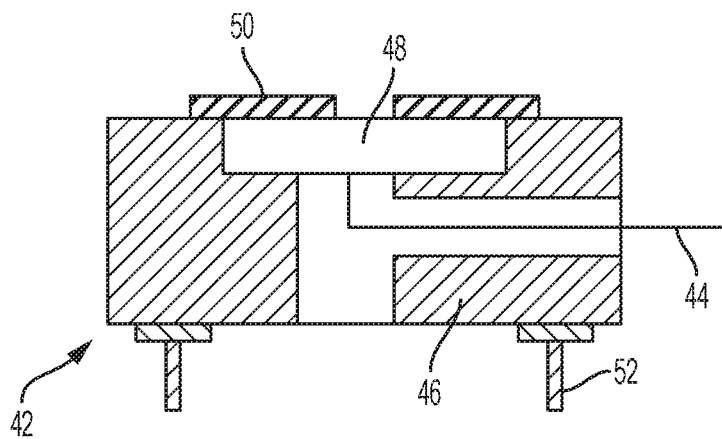
FIG. 7 is a cross-sectional view of an embodiment of an electrochemical cell base.

Referring now to FIGS. 1, 6, and 7, which illustrate a working electrode support 42 that enables electrochemical testing within the self-pressurized flow cell 16. The working electrode support 42 is comprised of a connector 44. The connector 44 may be made from the same material as a sample 48, whose corrosion properties are to be tested within the self-pressurized flow cell 16. Further, the connector 44 may be made from any conductive material or combination of conductive materials that can be connected to the sample 48 as a flat plate, a soldered joint, a wire, and combinations thereof. Examples of the sample 48 may include any conductive material, such as steel, copper, aluminum, platinum, gold, silver, iron, brass, bronze, alloys, and combinations thereof. The connector 44 is used to provide connection between the sample 48 and a potentiostat. In this embodiment, the sample 48 acts as either the anode or the cathode, depending on the polarization as defined by the electrochemical test being undertaken within the self-pressurized flow cell 16. For example, current may flow between the sample 48, the aqueous gas solution 19, and the counter electrode 38. The aqueous acid precursor 5 and the aqueous salt precursor 7 are introduced into the self-pressurized flow cell 16 as the precursor mixture 13 and then form the aqueous gas solution 19, which serves as the electrolyte. Electrochemical reactions then take place at the interface between the sample 48 and the aqueous gas solution 19 and between the aqueous gas solution 19 and the counter electrode 38.

To prepare for electrochemical testing, the sample 48 may be cast into a nonconductive mold 46, such as an epoxy mold, so that only a single, flat surface of known surface area of the sample 48 is exposed to the conditions of the self-pressurized flow cell 16. In one embodiment, a cover 50 is attached to the exposed surface of the sample 48. The cover 50 further defines the amount of surface area of the sample 48 that is exposed to the self-pressurized flow cell 16. This addition adds a degree of inter-experimental control to the sample 48 and further precludes interaction between the aqueous gas solution 19 and the corners or edges of the sample 48. In some embodiments, the cover 50 comprises an O-ring or another suitable material capable of defining the amount of exposed surface area of the sample 48.

The working electrode support 42 may further comprise a plurality of scanning electron microscopy (SEM) studs 52 that allow for reproducible orientation of the sample 48 and working electrode support 42 to allow for reproducible sample alignment for mapping before and after experimental tests are conducted.

In addition to electrochemical testing, the self-pressurized flow cell 16 of FIG. 1 may be modified for use in further characterization testing. One such characterization includes the ability to monitor weight changes of the sample 48. In this embodiment, a precise scale is placed under the self-pressurized flow cell 16 before the precursor mixture 13 has been introduced. Weights of the self-pressurized flow cell 16 are recorded for the duration of the experiment once the precursor mixture 13 has been introduced to the sample 48.

Further, the reacted aqueous gas stream 62 produced in the self-pressurized flow cell 16 may be subjected to in-line effluent analysis once it has exited the self-pressurized flow cell 16 via the outlet tube 20. In-line effluent analysis may be used to determine ion concentrations, such as for characterizing the corrosion products of the sample 48. Possible techniques for this type of characterization include optical spectrometry, inductively coupled plasma (ICP) atomic emission spectroscopy, pH measurements, UV-VIS spectroscopy, Fourier transform infrared spectroscopy, attenuated total reflection infrared spectroscopy, and any other suitable testing technique.

Referring now to FIG. 8, which depicts another embodiment of the apparatus 2 used to produce the reacted aqueous gas stream 62. In addition to the components described in the apparatus 2 of FIG. 1, additional components are described herein. Specifically, the sample 48 may either be embedded in the epoxy mold 46, as described above, or be free standing in the working electrode support 42. Further, the supplemental feed tube 36 may be attached to a syringe 54. The syringe 54 allows for specific concentrations of the aqueous acid precursor solution 5 or the aqueous salt precursor solution 7 to be added to the self-pressurized flow cell 16 to be added accurately and precisely. The syringe 54 may further comprise a backflow prevention valve 58 that ensures that the supplemental feed tube 36 inserted into the injection port 30 does not affect the sealing mechanism 18 of the self-pressurized flow cell 16. Finally, the pressure regulating device may be comprised of an outlet pump 56, a back pressure regulator 60, or combinations thereof. The outlet pump 56 further maintains the flow rate of the precursor mixture 13 through the self-pressurized flow cell 16 and the pressure within the self-pressurized flow cell 16.

Various method embodiments are considered suitable for producing the aqueous gas solution 19. One such method, in accordance with FIGS. 1-8 described above, may use salt-acidification reactions to generate specified quantities of the aqueous gas solution 19. The use of salt-acidification reactions allows for programmed, inter-experimental variations of gas concentrations while still maintaining other parameters, such as the concentration of ionic species in solution, within the self-pressurized flow cell 16, thereby overcoming the limitations of previous methods that rely solely on reaching saturation at a given pressure. For example, one such limitation is that the concentration of one gas species changes as saturation is reached for another gas species when additional species are added to the mixture, thereby causing the saturation conditions to change. The changing saturation conditions make it difficult to achieve desired concentrations of one species without altering the concentration of the other species if such a method is used to dissolve the gases into solution.

Here, the aqueous salt precursor solution 7 is acidified by the aqueous acid precursor solution 5 so as to produce the precursor mixture 13, which is introduced into the self-pressurized flow cell 16 as the aqueous gas solution 19. The aqueous gas solution 19 produced by these methods may comprise various gases and will preferably comprise carbon dioxide ($CO_2$) and hydrogen sulfide ($H_2S$), which are two gases of specific interest with regard to corrosion testing. Other gases produced may include hydrogen cyanide (HCN) and carbon monoxide (CO). These methods are particularly useful for producing and testing toxic gases, such as $H_2S$, because handling the aqueous salt and acid precursor solutions (5 and 7) is less hazardous than handling the gas itself. Further, the reacted aqueous gas stream 62 may be bubbled through a solution of base to neutralize any acid or dissolved $H_2S$ passed through the outlet tube 20 upon exiting the self-pressurized flow cell 16 so that the $H_2S$ gas is both generated and neutralized within the apparatus. Suitable bases may include sodium hydroxide (NaOH) and sodium hypochlorite (NaOCl).

The methods described above therefore provide in situ formation of precursor mixture 13 and neutralization of the reacted aqueous gas stream 62 within the self-pressurized flow cell 16, thereby effectively minimizing or altogether eliminating the need to transport, store, and handle potentially toxic gases.

Examples

The reaction to form $CO_2$ from the aqueous salt precursor solution and the aqueous acid precursor solution is described below in Reaction Mechanism 1:

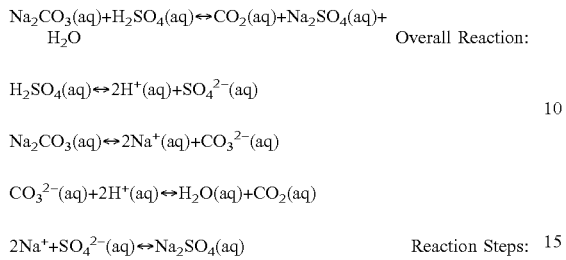

Overall Reaction:
$$Na_2CO_3(aq)+H_2SO_4(aq)\leftrightarrow CO_2(aq)+Na_2SO_4(aq)+H_2O$$

Reaction Steps:
$$H_2SO_4(aq)\leftrightarrow 2H^+(aq)+SO_4^{2-}(aq)$$
$$Na_2CO_3(aq)\leftrightarrow 2Na^+(aq)+CO_3^{2-}(aq)$$
$$CO_3^{2-}(aq)+2H^+(aq)\leftrightarrow H_2O(aq)+CO_2(aq)$$
$$2Na^++SO_4^{2-}(aq)\leftrightarrow Na_2SO_4(aq)$$

In this embodiment, sodium carbonate ($Na_2CO_3$) was used as the aqueous salt precursor solution and sulfuric acid ($H_2SO_4$) was used as the aqueous acid precursor solution to produce $CO_2$, sodium sulfate ($Na_2SO_4$), and water. The results of Reaction Mechanism 1 are shown below in Tables 1A and 1B:

TABLE 1A

| Precursor Solution | Compound Added | Concentration (mM) | | |
|---|---|---|---|---|
| | | Exp. 1 | Exp. 2 | Exp. 3 |
| A | $Na_2CO_3$ | 4 | 10 | 20 |
| | $Na_2SO_4$ | 16 | 10 | 0 |
| B | $H_2SO_4$ | 4 | 10 | 20 |

TABLE 1B

| Species | Concentration (mM) | | |
|---|---|---|---|
| | Exp. 1 | Exp. 2 | Exp. 3 |
| $CO_2$ | 2 | 5 | 10 |
| $Na^+$ | 20 | 20 | 20 |
| $SO_4^-$ | 10 | 10 | 10 |

Tables 1A and 1B show the precursor and final solution concentrations for different concentrations of the aqueous $CO_2$, which was produced in three separate experiments. The $CO_2$ concentrations ranged from 2 mM to 10 mM. These experiments were performed at 25° C. at a total flow rate of 20 mL/min (10 mL/min for each precursor solution). The resulting pressure produced in the self-pressurized flow cell 16 varied between the three different experimental tests detailed in Tables 1A and 1B, with the pressure being related to the concentration of $CO_2$ comprising the aqueous gas stream. The greater the amount of $CO_2$ comprising the aqueous gas stream meant a higher concentration of $CO_2$ gas in the experiment, which caused a higher total pressure within the cell.

The results indicate that aqueous gas concentrations may be chosen by controlling the ratio of acid to salt in the precursor solutions. Here, the volumetric ratio of acid to salt was 1:1. As a result, the aqueous gas concentrations ranged from lower than atmospheric concentrations to as high, or even higher, than saturated conditions depending on precursor solubility limits. The use of strong acid as the aqueous acid precursor solution, such as $H_2SO_4$, ensured that the aqueous acid precursor solution ions fully dissociated to form the desired aqueous gas stream at the concentration of the limiting reagent (here, the limiting reagents were $Na_2CO_3$ and $H_2SO_4$). As noted above, other strong acids, such as HCl, may also be used as the aqueous acid precursor solution, thereby providing flexibility over the chemical identity of the counter ions present in solution.

The reaction to form $H_2S$ from the aqueous salt precursor solution and the aqueous acid precursor solution is described below in Reaction Mechanism 2:

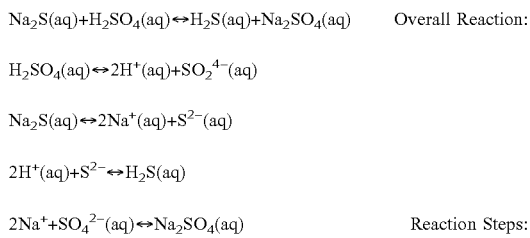

Overall Reaction:
$$Na_2S(aq)+H_2SO_4(aq)\leftrightarrow H_2S(aq)+Na_2SO_4(aq)$$

Reaction Steps:
$$H_2SO_4(aq)\leftrightarrow 2H^+(aq)+SO_2^{4-}(aq)$$
$$Na_2S(aq)\leftrightarrow 2Na^+(aq)+S^{2-}(aq)$$
$$2H^+(aq)+S^{2-}\leftrightarrow H_2S(aq)$$
$$2Na^++SO_4^{2-}(aq)\leftrightarrow Na_2SO_4(aq)$$

In this embodiment, sodium sulfide ($Na_2S$) was used as the aqueous salt precursor solution and sulfuric acid ($H_2SO_4$) was used as the aqueous acid precursor solution to produce $H_2S$, $Na_2SO_4$, and water. The results of Reaction Mechanism 2 are shown below in Tables 2A and 2B:

TABLE 2A

| Precursor Solution | Compound Added | Concentration (mM) | | |
|---|---|---|---|---|
| | | Exp. 1 | Exp. 2 | Exp. 3 |
| A | $Na_2S$ | 4 | 10 | 20 |
| | $Na_2SO_4$ | 16 | 10 | 0 |
| B | $H_2SO_4$ | 4 | 10 | 20 |

TABLE 2B

| Species | Concentration (mM) | | |
|---|---|---|---|
| | Exp. 1 | Exp. 2 | Exp. 3 |
| $H_2S$ | 2 | 5 | 10 |
| $Na^+$ | 20 | 20 | 20 |
| $SO_4^-$ | 10 | 10 | 10 |

Tables 2A and 2B show the precursor and final solution concentrations for different concentrations of the aqueous $H_2S$, which was produced in three separate experiments. The $H_2S$ concentrations range from 2 mM to 10 mM. The pressure varied between the three different experimental tests detailed in Tables 2A and 2B, with the pressure being related to the concentration of $H_2S$ comprising the aqueous gas stream. The greater the amount of $H_2S$ comprising the aqueous gas stream meant a higher concentration of $H_2S$ gas in the experiment, which caused a higher total pressure within the cell.

As noted above, these results indicate that aqueous gas concentrations may be chosen by controlling the ratio of acid to salt in the precursor solutions. Here, the volumetric ratio of acid to salt was again 1:1. Therefore, the aqueous gas concentrations may again range from lower than atmospheric concentrations to as high, or even higher, than saturated conditions depending on precursor solution solubility limits. The total pressure of the experiment was dependent on the conditions of interest that were trying to be duplicated. Because the cell was self-pressurizing in the prior examples, the pressure of the cell was determined by the concentration of the aqueous gas being studied.

In further experiments, additional salts were added to the aqueous salt precursor solution to ensure that the concentration of ions in the self-pressurized flow cell remained constant regardless of the change in the aqueous gas concentration between experiments. Such control is seen in Tables 1A, 1B, 2A, and 2B above, where the addition of $Na_2SO_4$ to the aqueous salt precursor solution allowed the final $Na_2SO_4$ concentration to be consistent, despite the changes in $H_2S$ and $CO_2$ concentrations.

Tables 3A and 3B, below, show the same CO2 concentrations as Tables 1A and 1B, but with the addition of additional salts to the aqueous salt precursor solution in order to simulate the conditions experienced by pipes in the presence of oil well formation water. In addition to the $Na_2CO_3$ and the $Na_2SO_4$ shown in Tables 1A and 1B and Equation 1, the aqueous salt precursor solution of Tables 3 and 3B further comprise magnesium chloride (MgCl), calcium chloride (CaCl), and potassium chloride (KCl):

TABLE 3A

| Precursor Solution | Compound Added | Concentration (mM) | | |
|---|---|---|---|---|
| | | Exp. 1 | Exp. 2 | Exp. 3 |
| A | $Na_2CO_3$ | 4 | 10 | 20 |
| | $Na_2SO_4$ | 16 | 10 | 20 |
| | MgCl | 2 | 2 | 2 |
| | CaCl | 6 | 6 | 6 |
| | KCl | 1 | 1 | 1 |
| B | $H_2SO_4$ | 4 | 10 | 20 |

TABLE 3B

| Species | Concentration (mM) | | |
|---|---|---|---|
| | Exp. 1 | Exp. 2 | Exp. 3 |
| $CO_2$ | 2 | 5 | 10 |
| $Na^+$ | 20 | 20 | 20 |
| $SO_4^-$ | 10 | 10 | 10 |
| $Mg^+$ | 1 | 1 | 1 |
| $Ca^+$ | 3 | 3 | 3 |
| $K^+$ | 0.5 | 0.5 | 0.5 |
| $Cl^-$ | 4.5 | 4.5 | 4.5 |

While the above examples disclosed in Tables 1A, 1B, 2A, and 2B incorporated methods utilizing a 1:1 volumetric ratio of aqueous acid precursor solution to aqueous salt precursor solution, further embodiments disclosed in Tables 3A and 3B show other volumetric ratios of aqueous acid precursor solution to aqueous salt precursor solution. Indeed, no required volumetric ratio of aqueous acid precursor solution to aqueous salt precursor solution was required to achieve production of the aqueous gas stream. As a result, one aqueous precursor solution comprised the majority of the volume of the aqueous gas stream, as long as the other aqueous precursor solutions were appropriately concentrated and pumped at appropriate rates into the self-pressurized flow cell.

This flexibility in the volumetric ratio between the aqueous acid precursor solution to the aqueous salt precursor solution is especially useful for experiments such as a brine field simulation, where solubility limits may prevent all of the salt from dissolving in the aqueous salt precursor solution that only contained one-half of the final solution volume of the aqueous gas stream. In such a case, the volume of the aqueous salt precursor solution could be much larger than the volume of the aqueous acid precursor solution so long as the aqueous acid precursor solution is appropriately more concentrated than the aqueous salt precursor solution. Tables 4A and 4B, below, disclose the same final ion concentration when producing aqueous CO2 as was shown in Tables 1A and 1B, but where the volume of the aqueous salt precursor solution was two times the volume of the aqueous acid precursor solution. The concentration of CO2 is increased from left to right in Table 4B, while the concentration of the other species in solution is maintained constant:

TABLE 4A

| Precursor Solution | Compound Added | Concentration (mM) | | |
|---|---|---|---|---|
| | | Exp. 1 | Exp. 2 | Exp. 3 |
| A | $Na_2CO_3$ | 3 | 7.5 | 15 |
| | $Na_2SO_4$ | 12 | 7.5 | 0 |
| B | $H_2SO_4$ | 6 | 15 | 30 |

TABLE 4B

| Species | Concentration (mM) | | |
|---|---|---|---|
| | Exp. 1 | Exp. 2 | Exp. 3 |
| $CO_2$ | 2 | 5 | 10 |
| $Na^+$ | 20 | 20 | 20 |
| $SO_4^-$ | 10 | 10 | 10 |

The mass of precursor solution chemicals present in various concentrations of $CO_2$ and $H_2S$ that comprise aqueous gas streams are shown below in Table 5:

TABLE 5

| | | $CO_2$ (in µM) | | | | $H_2S$ (in µM) | | | |
|---|---|---|---|---|---|---|---|---|---|
| | | 10,000 | 5,000 | 100 | 5 | 10,000 | 5,000 | 100 | 5 |
| | | Mass in solution (g/L) | | | | | | | |
| Chemical | $H_2SO_4$ | 0.981 | 0.490 | 0.010 | 0.0005 | 0.981 | 0.490 | 0.010 | 0.0005 |
| | $Na_2S$ | 0 | 0 | 0 | 0 | 0.780 | 0.390 | 0.008 | 0.0004 |
| | $Na_2CO_3$ | 1.060 | 0.530 | 0.011 | 0.001 | 0 | 0 | 0 | 0 |
| | $Na_2SO_4$ | 0 | 0.710 | 1.406 | 1.420 | 0 | 0.710 | 1.406 | 1.420 |

Ionic species masses for various concentrations of $CO_2$ and $H_2S$ that comprise aqueous gas streams are shown below in Table 6. It is noted that peripheral species concentrations are maintained across experiments while gas concentrations are varied:

TABLE 6

| | | $CO_2$ (in µM) | | | | $H_2S$ (in µM) | | | |
|---|---|---|---|---|---|---|---|---|---|
| | | 10,000 | 5,000 | 100 | 5 | 10,000 | 5,000 | 100 | 5 |
| | | | | | Mass in solution (g/L) | | | | |
| Ionic Species | $Na^+$ | 0.460 | 0.460 | 0.460 | 0.460 | 0.460 | 0.460 | 0.460 | 0.460 |
| | $SO_4^{2-}$ | 0.961 | 0.961 | 0.961 | 0.961 | 0.961 | 0.961 | 0.961 | 0.961 |
| | $H_2^+$ | 0.010 | 0.005 | 0.0001 | 0.000005 | 0.010 | 0.005 | 0.0001 | 0.000005 |
| | $CO_3^{2-}$ | 0.600 | 0.300 | 0.006 | 0.0003 | 0 | 0 | 0 | 0 |
| | $S^{2-}$ | 0 | 0 | 0 | 0 | 0.321 | 0.160 | 0.003 | 0.0002 |

Figure 9:
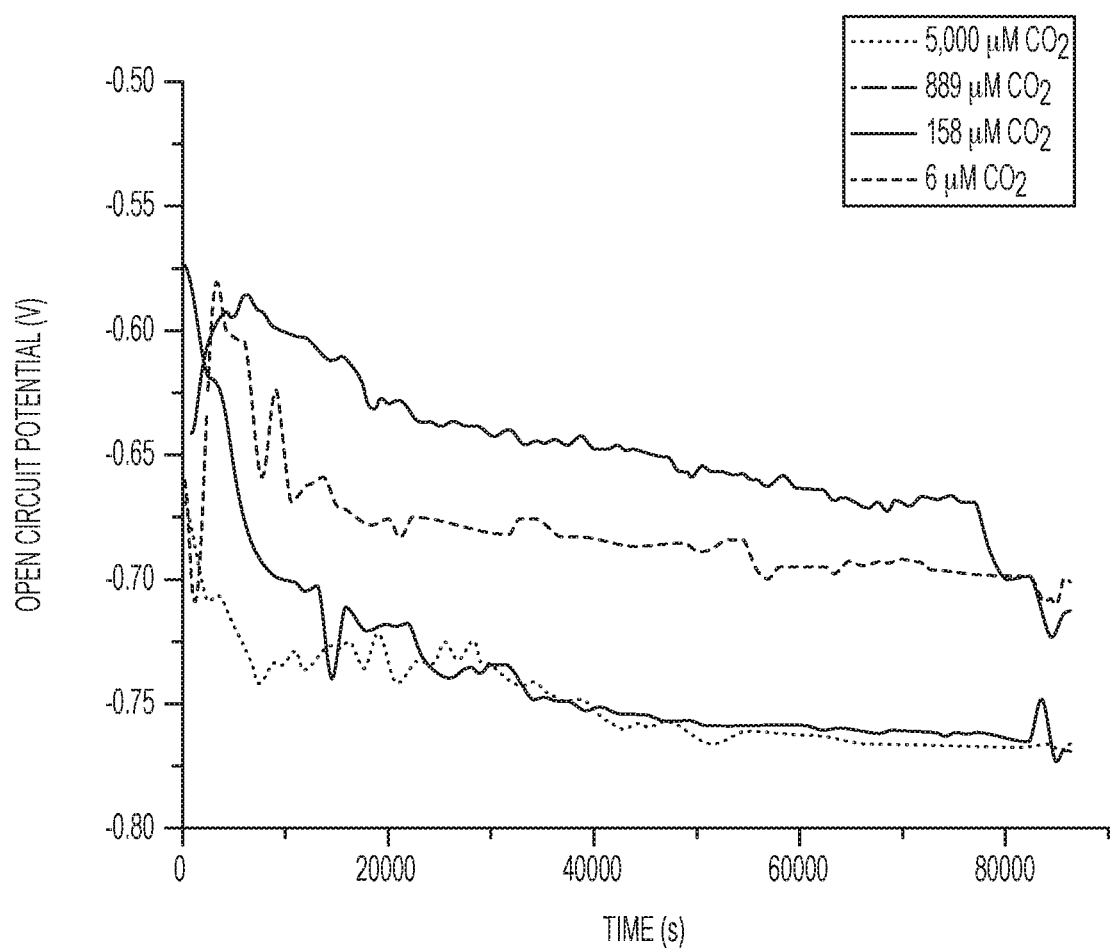
FIG. 9 is a graph that depicts electrochemical data of steel exposed to various controlled $CO_2$ concentrations over a 24 hour period of experimentation within the self-pressurized flow cell.

As described above, corrosion testing of the samples exposed to aqueous gas streams within the self-pressurized flow cell is critical. FIG. 9 is a graph that depicts electrochemical data of steel exposed to various controlled $CO_2$ concentrations over a 24 hour period of experimentation within the self-pressurized flow cell. The open circuit potential measurements are correlated to the corrosion rate of the sample. Therefore, the data can be extrapolated and used to determine information about the corrosion behavior of the sample when the sample is exposed to corrosive aqueous gases like $CO_2$.

It will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these aspects.

What is claimed is:

1. A method for generating an aqueous gas solution comprising dissolved gas in an aqueous stream, the method comprising:
    mixing an aqueous acid precursor solution and an aqueous salt precursor solution at an in-line mixing location to produce a liquid precursor mixture, wherein both the aqueous acid precursor solution and the aqueous salt precursor solution are fed under pressure through individual inlet pumps upstream of the in-line mixing location;
    introducing the liquid precursor mixture under pressure through an inlet tube of a self-pressurized flow cell downstream of the in-line mixing location, wherein the inlet tube is surrounded by a sealing mechanism to maintain pressure within the self-pressurized flow cell; and
    allowing the reaction of the aqueous acid precursor and the aqueous salt precursor to generate the aqueous gas solution and produce a pressure level that correlates to an amount of dissolved gas produced once in the self-pressurized flow cell;
    wherein the dissolved gas comprises carbon dioxide, hydrogen sulfide, or a combination of both;
    wherein the aqueous gas solution undergoes real-time testing within the self-pressurized flow cell; and
    wherein the real-time testing comprises corrosion testing.

2. The method for generating an aqueous gas solution of claim 1, wherein the real-time testing further comprises electrochemical measurements, pH measurements, ultraviolet-visible (UV-VIS) spectroscopy, weight loss or combinations thereof.

3. The method for generating an aqueous gas solution of claim 1, wherein the aqueous gas solution is reacted with a sample, thereby producing a reacted aqueous gas stream.

4. The method for generating an aqueous gas solution of claim 3, wherein the sample comprises conductive material.

5. The method for generating an aqueous gas solution of claim 4, wherein the conductive material comprises steel, copper, aluminum, platinum, gold, silver, iron, brass, bronze, alloys, or combinations thereof.

6. The method for generating an aqueous gas solution of claim 3, wherein the reacted aqueous gas stream undergoes testing comprising optical spectrometry or inductively coupled plasma (ICP) atomic emission spectroscopy or Fourier transform infrared spectroscopy, attenuated total reflection infrared spectroscopy, once the aqueous gas stream reacts with the sample and is transferred from the self-pressurized flow cell through an outlet tube.

7. The method for generating an aqueous gas solution of claim 6, wherein the reacted aqueous gas stream is transferred from the self-pressurized flow cell through an outlet tube.

8. The method for generating an aqueous gas solution of claim 7, wherein the reacted gas stream is further bubbled through a basic solution.

9. The method for generating an aqueous gas solution of claim 6, wherein the outlet tube further comprises a pressure regulating device that prevents depressurization of the self-pressurized flow cell.

10. The method for generating an aqueous gas solution of claim 9, wherein the pressure regulating device comprises an outlet pump, a back pressure regulator, or combinations thereof.

11. The method for generating an aqueous gas solution of claim 1, wherein the aqueous acid precursor solution comprises sulfuric acid, hydrogen iodide, hydrogen bromide, perchloric acid, hydrogen chloride, chloric acid, nitric acid, or combinations thereof.

12. The method for generating an aqueous gas solution of claim 1, wherein the aqueous acid precursor solution has a concentration of between 5 µM and 10 M.

13. The method for generating an aqueous gas solution of claim 1, wherein the aqueous acid precursor solution has a concentration of between 100 µM and 100 mM.

14. The method for generating an aqueous gas solution of claim 1, wherein the aqueous salt precursor solution comprises sodium sulfide, sodium carbonate, or a combination thereof.

15. The method of claim 14, wherein the aqueous salt precursor solution further comprises sodium sulfate, magnesium chloride, calcium chloride, potassium chloride, and combinations thereof.

16. The method for generating an aqueous gas solution of claim 1, wherein the aqueous salt precursor solution has a concentration of between 5 μM and 10 M.

17. The method for generating an aqueous gas solution of claim 1, wherein the aqueous salt precursor solution has a concentration of between 100 μM and 100 mM.

18. The method for generating an aqueous gas solution of claim 1, wherein the sealing mechanism comprises an injection port, an inlet port, an outlet port, a counter electrode port, a reference electrode port, or combinations thereof.

19. The method for generating an aqueous gas solution of claim 1, wherein the sealing mechanism further comprises an inner portion and an outer portion.

20. The method for generating an aqueous gas stream of claim 19, wherein the inner portion further comprises a PEEK rod.

21. The method for generating an aqueous gas solution of claim 19, wherein the outer portion further comprises a stopper made from EPDM rubber, silicone rubber, neoprene rubber, pure gum rubber, natural rubber, butyl rubber, nitrile rubber, or any other suitable rubber or non-rubber materials.

* * * * *